US009428431B2

(12) United States Patent
Bab et al.

(10) Patent No.: US 9,428,431 B2
(45) Date of Patent: Aug. 30, 2016

(54) COMPOSITIONS COMPRISING CB RECEPTOR AGONISTS, USES THEREOF AND METHODS FOR THEIR PREPARATION

(75) Inventors: Itai Bab, Carmei Yossef (IL); Raphael Mechoulam, Jerusalem (IL); Aviva Breuer, Jerusalem (IL); Naama Mussai, Jerusalem (IL)

(73) Assignee: Yissum Research Development Company of the Hebrew University of Jerusalem, Ltd., Jerusalem (IL)

(*) Notice: Subject to any disclaimer, the term of this patent is extended or adjusted under 35 U.S.C. 154(b) by 508 days.

(21) Appl. No.: 13/122,662

(22) PCT Filed: Oct. 11, 2009

(86) PCT No.: PCT/IL2009/000964
§ 371 (c)(1),
(2), (4) Date: Jul. 20, 2011

(87) PCT Pub. No.: WO2010/041253
PCT Pub. Date: Apr. 15, 2010

(65) Prior Publication Data
US 2011/0269842 A1 Nov. 3, 2011

Related U.S. Application Data

(60) Provisional application No. 61/103,054, filed on Oct. 6, 2008, provisional application No. 61/165,011, filed on Mar. 31, 2009.

(51) Int. Cl.
| | | |
|---|---|---|
| C07C 43/23 | (2006.01) | |
| C07C 67/14 | (2006.01) | |
| C07C 67/29 | (2006.01) | |
| C07C 67/293 | (2006.01) | |
| C07C 41/26 | (2006.01) | |

(52) U.S. Cl.
CPC ............ *C07C 43/23* (2013.01); *C07C 41/26* (2013.01); *C07C 67/14* (2013.01); *C07C 67/29* (2013.01); *C07C 67/293* (2013.01); *C07B 2200/07* (2013.01); *C07C 2101/16* (2013.01); *C07C 2102/42* (2013.01)

(58) Field of Classification Search
CPC ....... C07C 41/26; C07C 43/23; C07C 67/14; C07C 67/29; C07C 67/293; C07C 69/24; C07C 2101/16; C07C 2102/42; C07C 2101/42; C07B 2200/07
USPC .......................................... 514/729; 568/823
See application file for complete search history.

(56) References Cited

U.S. PATENT DOCUMENTS

| | | | |
|---|---|---|---|
| 4,282,248 A | | 8/1981 | Mechoulam et al. |
| 5,434,295 A | * | 7/1995 | Mechoulam et al. ........ 560/141 |
| 6,864,291 B1 | | 3/2005 | Fride et al. |
| 2007/0248702 A1 | | 10/2007 | Fernandez-Ruiz |

FOREIGN PATENT DOCUMENTS

| | | |
|---|---|---|
| WO | 03/005960 A2 | 1/2003 |
| WO | 2004/103410 A1 | 12/2004 |

OTHER PUBLICATIONS

Bonnelli et. al., Expert Opinion in Pharmacotherapy, 2007, Informa UK Ltd, vol. 8, issue 2, pp. 141-153.*
Chabner et. al., Nature Reviews Cancer, 2005, Nature Publishing Group, vol. 5, pp. 65-72.*
Leaf, Fortune, Mar. 9 2004, Time Inc., pp. 1-29.*
Lindvall et. al., Nature, 2006, Nature Publishing Group, vol. 441, pp. 1094-1096.*
Singh et. al., Progress in Neurobiology, 2007, Elsevier, vol. 81, pp. 29-44.*
Hanus, et al., "HU-308: A specific agonist for CB2, a peripheral cannabinoid receptor", PNAS, vol. 96, No. 25, pp. 14228-14233, (1999).
Ofek, et al., "Peripheral cannabinoid receptor, CB2, regulates bone mass", PNAS, vol. 103, No. 3, pp. 696-701, (2006).
Bab, et al., "Endocannabinoids and the Regulation of Bone Metabolism", Journal of Neuroendocrinology, vol. 20, Suppl. 1, pp. 69-74, (2008).
Hanus, et al., "Enantiomeric cannabidiol derivatives: synthesis and binding to cannabinoid receptors", Org. Biomol. Chem., vol. 3, pp. 1116-1123, (2005).
Devane, et al., "Isolation and Structure of a Brain Constituent That Binds to the Cannabinoid Receptor", Science, vol. 258, pp. 1946-1949, (1992).
Munro, et al., "Molecular characterization of a peripheral receptor for cannabinoids", Nature, vol. 365, pp. 61-65, (1993).
San Miguel, et al., "ERK1/2-activated de Novo Mapkapk2 Synthesis is Essential for Osteogenic Growth Peptide Mitogenic Signaling in Osteoblastic Cells", The Journal of Biological Chemistry, vol. 280, No. 45, pp. 37495-37502, (2005).
Alexander, et al., "Human Parathyroid Hormone 1-34 Reverses Bone Loss in Ovariectomized Mice", Journal of Bone and Mineral Research, vol. 16, No. 9, pp. 1665-1673, (2001).
Benito, et al., "Cannabinoid CB2 receptors in human brain inflammation", British Journal of Pharmacology, vol. 153, pp. 277-285, (2008).
Docagne, et al., "Therapeutic potential of CB2 targeting in multiple sclerosis", Expert Opin. Ther. Targets, vol. 12, No. 2, pp. 185-195, (2008).
Kim, et al., "AM1241, a cannabinoid CB2 receptor selective compound, delays disease progression in a mouse model of amyotrophic lateral sclerosis", European Journal of Pharmacology, vol. 542, pp. 100-105, (2006).
Benito, et al., "A Glial Endogenous Cannabinoid System is Upregulated in the Brains of Macaques with Simian Immunodeficiency Virus-Induced Encephalitis", The Journal of Neuroscience, vol. 25, No. 10, pp. 2530-2536, (2005).

(Continued)

*Primary Examiner* — Sarah Pihonak
(74) *Attorney, Agent, or Firm* — Vorys, Sater, Seymour & Pease LLP (57) ABSTRACT

Provided are compositions including (3R, 4R, 6R)-stereoisomers of phenyl substituted pinenes having CB receptor agonist properties, methods of treating diseases or disorders with the pharmaceutical compositions, and processes for their preparation are also provided.

14 Claims, 2 Drawing Sheets

(56) References Cited

OTHER PUBLICATIONS

Zhang, et al., "Induction of CB2 receptor expression in the rat spinal cord of neuropathic but not inflammatory chronic pain models", European Journal of Neuroscience, vol. 17, pp. 2750-2754, (2003).

Sagredo, et al., "Cannabinoid CB2 receptor agonists protect the striatum against malonate toxicity: relevance for Huntington's disease", Glia, vol. 57, No. 11, pp. 1154-1167, (2009).

Papa, "The cannabinoid system in Parkinson's disease: Multiple targets to motor effects", Experimental Neurology, vol. 211, pp. 334-338, (2008).

Agid, et al., "Emerging drugs for schizophrenia", Expert Opin. Emerging Drugs, vol. 13, No. 3, pp. 479-495, (2008).

Magen, et al., "Endocannabinoids in Liver Disease and Hepatic Encephalopathy", Current Pharmaceutical Design, vol. 14, pp. 2362-2369, (2008).

Zhang, et al., "Modulation of the Balance Between Cannabinoid CB1 and CB2 Receptor Activation During Cerebral Ischemic/Reperfusion Injury", Neuroscience, vol. 152, No. 3, pp. 753-760, (2008).

Levin, et al., "Structural Features Affecting Chiral Resolution of Cannabimimetic Enantiomers by Amylose 3,5-Dimethylphenylcarbamate Chiral Stationary Phase", Chirality, vol. 7, pp. 140-146, (1995).

Mechoulam, et al., "Cannabimimetic Activity of Novel Enantiomeric, Benzofuran Cannabinoids", J. Med. Chem., vol. 33, pp. 1037-1043, (1990).

\* cited by examiner

COMPOSITIONS COMPRISING CB RECEPTOR AGONISTS, USES THEREOF AND METHODS FOR THEIR PREPARATION

This is a National Phase Application filed under 35 U.S.C. §371 as a national stage of PCT/IL2009/000964, filed on Oct. 11, 2009, an application claiming the benefit under 35 USC 119(e) of U.S. Provisional Application No. 61/103,054, filed on Oct. 6, 2008, and an application claiming the benefit under 35 USC 119(e) of U.S. Provisional Application No. 61/165,011, filed on Mar. 31, 2009, the content of each of which is hereby incorporated by reference in its entirety.

FIELD OF THE INVENTION

This invention relates to compositions comprising diastereomeric CB receptor agonists, uses thereof and methods of their preparation.

BACKGROUND OF THE INVENTION

The following publications are relevant for describing the state of the art in the field of the invention
1. L. Hanus, et al. *Proc. Natl. Acad. Sci, U.S.A.* 96:14228-14233, 1999.
2. O. Ofek, et al. *Proc. Natl. Acad. Sci. U.S.A.* 103:696-701, 2006.
3. I. Bab, et al. *J. Neuroendocrinol.* 20 Suppl 1:69-74, 2008.
4. L. Hanus, et al. *Org. Biomol. Chem.* 3:1116-1123, 2005.
5. W. A. Devane, et al. *Science.* 258:1946-1949, 1992.
6. S. Munro, et al. *Nature.* 365:61-65, 1993.
7. S. M. Miguel, et al. *J. Biol. Chem.* 280:37495-37502, 2005.
8. J. M. Alexander, et al. *J. Bone Min. Res.* 16:1665-1673, 2001.
9. I. Bab, et al. WO 2004/103,410
10. E. Fride et al. U.S. Pat. No. 6,864,291
11. R. Mechoulam et al. U.S. Pat. No. 5,434,295

In vertebrates, skeletal mass is determined by continuous remodeling consisting of the concerted and balanced action of osteoclasts, the bone resorbing cells, and osteoblasts, the bone forming cells.

Osteoporosis, the most prevalent degenerative disease in developed countries, results from the impairment of this balance, leading to bone loss and increased fracture risk. We have recently reported the expression of functional type 2 cannabinoid receptor (CB2) in bone cells.

The CB2 specific agonist HU-308 (WO 2004/103410; Hanuš et al, 1999), stimulates in vitro osteoblastogenesis and inhibits osteoclastogenesis. In mice, HU-308 stimulates bone formation and inhibits bone resorption, thus attenuating ovariectomy (OVX)-induced bone loss (Ofek et al, 2006). In another mouse model it rescues OVX-induced bone loss (Bab et al, 2008).

SUMMARY OF THE INVENTION

The compound of general formula (I):

comprises three stereogenic centers, namely: carbon atom in position 3, carbon atom in position 4 and carbon atom in position 6 (substituents $R_1$, $R_6$, $R_7$ and $R_9$ are defined herein below). Thus, compound of general formula (I) may exist in any one of the stereoisomeric forms, indicated in Table 1 below.

TABLE 1

CIP configuration of diastereomers of compounds of general formula (I)

| Stereoisomer No. | CIP configuration of position 3 | CIP configuration of position 4 | CIP configuration of position 6 |
|---|---|---|---|
| 1 (HU-433) | R | R | R |
| 2 | S | R | R |
| 3 | R | S | S |
| 4 (HU-308) | S | S | S |
| 5 | R | R | S |
| 6 | S | R | S |
| 7 | R | S | R |
| 8 | S | S | R |

However, it is noted that since positions 4 and 6 are both located at the bridgeheads of the bicyclic ring system, their stereochemistry is interconnected and diastereomers (3R, 4R, 6S), (3S, 4R, 6S), (3R, 4S, 6R) and (3S, 4S, 6R) (corresponding to diastereomers 5, 6, 7 and 8 in above table) do not exist under typical processing and thermal conditions.

U.S. Pat. No. 6,864,291 disclosed a compound of general formula (I) having a configuration of (3S, 4S) (HU-308) being essentially free from its only enantiomer (having (3R, 4R) configuration), compositions and uses thereof.

The compound of general formula (I'):

comprises four stereogenic centers, namely: carbon atom in position 1, carbon atom in position 3, carbon atom in position 4 and carbon atom in position 6 (substituents $R_1$, $R_6$, $R_7$ and $R_9$ are defined herein below). Thus, compound of general formula (I') may exist in any one of the stereoisomeric forms, indicated in Table 2 below.

TABLE 2

CIP configuration of diastereomers of compounds of general formula (I')

| Stereoisomer No. | CIP configuration of position 1 | CIP configuration of position 3 | CIP configuration of position 4 | CIP configuration of position 6 |
|---|---|---|---|---|
| 1 | R | R | R | R |
| 2 | S | R | R | R |
| 3 | R | S | R | R |
| 4 | S | S | R | R |
| 5 | R | R | S | S |
| 6 | S | R | S | S |
| 7 | R | S | S | S |

TABLE 2-continued

CIP configuration of diastereomers
of compounds of general formula (I')

| Stereoisomer No. | CIP configuration of position 1 | CIP configuration of position 3 | CIP configuration of position 4 | CIP configuration of position 6 |
|---|---|---|---|---|
| 8 | S | S | S | S |
| 9 | R | R | R | S |
| 10 | S | R | R | S |
| 11 | R | S | R | S |
| 12 | S | S | R | S |
| 13 | R | R | S | R |
| 14 | S | R | S | R |
| 15 | R | S | S | R |
| 16 | S | S | S | R |

However, it is noted that since positions 4 and 6 are both located at the bridgeheads of the bicyclic ring system, their stereochemistry is interconnected and diastereomers (1R, 3R, 4R, 6S), (1S, 3R, 4R, 6S), (1R, 3S, 4R, 6S), (1S, 3S, 4R, 6S), (1R, 3R, 4S, 6R), (1S, 3R, 4S, 6R), (1R, 3S, 4S, 6R) and (1S, 3S, 4S, 6R) (corresponding to stereoisomers 9, 10, 11, 12, 13, 14, 15, 16 in Table 2 above) do not exist under typical processing and thermal conditions.

The present invention provides a composition comprising the (3R, 4R, 6R)-diastereomer of a compound of general formula (II):

(II)

said composition having diastereomeric ratio of between about 50%:50% to about 100%:0%; wherein ===== is a single or double bond;

$R_1$ is independently selected from —$R_2OR_3$, —C(=O)$R_4$, —OC(=O)$R_5$;

$R_2$ is a $C_1$-$C_5$ straight or branched alkylene;

$R_3$ is selected from the group consisting of H, —C(=O)OH, straight or branched $C_1$-$C_5$ alkyl, straight or branched $C_1$-$C_5$ acyl, straight or branched $C_1$-$C_5$ amide;

$R_4$, and $R_5$ are independently selected from the group consisting of H, OH, straight or branched $C_1$-$C_5$ alkyl, straight or branched $C_1$-$C_5$ alkoxy, straight or branched $C_1$-$C_5$ amine;

$R_6$ and $R_7$ are each independently selected from H, and —$OR_8$ wherein $R_8$ is a straight or branched $C_1$-$C_5$ alkyl, provided that at least one of $R_6$ and $R_7$ is different than H (i.e. provided that at least one of $R_6$ and $R_7$ is —$OR_8$); and $R_9$ is independently selected from an optionally substituted straight or branched $C_6$-$C_{12}$ alkyl, an optionally substituted straight or branched $C_5$-$C_9$ alkoxy, an optionally substituted straight or branched $C_1$-$C_7$ ether.

In a further aspect, the invention provides a composition comprising the (3R, 4R, 6R)-diastereomer of a compound of general formula (II), said composition having diatereomeric excess of between about 0% to about 100%; wherein ===== is a single or double bond; $R_1$ is independently selected from —$R_2OR_3$, —C(=O)$R_4$, —OC(=O)$R_5$; $R_2$ is a $C_1$-$C_5$ straight or branched alkylene; $R_3$ is selected from the group consisting of H, straight or branched $C_1$-$C_5$ alkyl, straight or branched $C_1$-$C_5$ acyl, straight or branched $C_1$-$C_5$ amide; $R_4$, and $R_5$ are independently selected from the group consisting of H, OH, straight or branched $C_1$-$C_5$ alkyl, straight or branched $C_1$-$C_5$ alkoxy, straight or branched $C_1$-$C_5$ amine; $R_6$ and $R_7$ are each independently selected from H, and —$OR_8$ wherein $R_8$ is a straight or branched $C_1$-$C_5$ alkyl, provided that at least one of $R_6$ and $R_7$ is different than H; and $R_9$ is independently selected from an optionally substituted straight or branched $C_6$-$C_{12}$ alkyl, an optionally substituted straight or branched $C_5$-$C_9$ alkoxy, an optionally substituted straight or branched $C_1$-$C_7$ ether.

It is noted that in an embodiment where $R_1$ is —$R_2OR_3$, $R_2$ is a $C_1$-$C_5$ straight or branched alkylene and $R_3$ is selected from the group consisting of H (i.e. leading to a substitution with an alcohol group), straight or branched $C_1$-$C_5$ alkyl (i.e. leading to a substitution with an ether group), straight or branched $C_1$-$C_5$ acyl (i.e. leading to a substitution with an ester group), —C(=O)OH (i.e. leading to a substitution with a —$C_1$-$C_5$ alkyl-OC(=O)OH group) and a straight or branched $C_1$-$C_5$ amide (i.e. leading to a substitution with an amide ester group).

In another embodiment where $R_1$ is —C(=O)$R_4$, $R_4$ is selected from a group consisting of H (i.e. leading to a substitution with an aldehyde group); OH, (i.e. leading to a substitution with an acetic acid group), straight or branched $C_1$-$C_5$ alkyl (i.e. leading to a substitution with a ketone group), straight or branched $C_1$-$C_5$ alkoxy (i.e. leading to a substitution by a —C(=O)OR group) and a straight or branched $C_1$-$C_5$ amine (i.e. leading to a substitution by a —C(=O)NHR or —C(=O)NR'R' group).

In a further embodiment where $R_1$ is —OC(=O)$R_5$, $R_5$ is selected from a group consisting of H (i.e. leading to a substitution with an aldehyde group); OH (i.e. leading to a substitution with an —OC(=O)OH group), straight or branched $C_1$-$C_5$ alkyl (i.e. leading to a substitution with a —OC(=O)R group), straight or branched $C_1$-$C_5$ alkoxy (i.e. leading to a substitution by a —OC(=O)OR group) and a straight or branched $C_1$-$C_5$ amine (i.e. leading to a substitution by a —OC(=O)NHR or —OC(=O)NRR' group).

In one embodiment of the present invention ===== is a double bond. Thus, a compound of formula (II) is:

(III)

wherein $R_1$, $R_6$, $R_7$, and $R_9$ are have the same meaning as defined hereinabove.

In another embodiment of the present invention ===== is a single bond. Thus, a compound of formula (II) is:

(IV)

wherein $R_1$, $R_6$, $R_7$, and $R_9$ are have the same meaning as defined hereinabove.

The term "diastereomeric ratio" as used herein is meant to encompass the ratio of the percentage of one diastereoisomer in a mixture to that of another diastereoisomer of a compound of formula (I).

Thus, in one embodiment when ===== indicates a double bond, said diastereomeric ratio indicates the percentage ratio between (3R, 4R, 6R)-diastereomer of a compound of general formula (I) (compound of formula (III)), and each of (3S, 4R, 6R)- or (3R, 4S, 6S)-diastereomers, all of which (together or individually) may be present in said composition of the invention.

When a composition of the invention has a diastereomeric ratio of 50%:50%, it should be understood that the ratio between the (3R, 4R, 6R)-diastereomer of a compound of general formula (I) (compound of formula (III)) and any one of the diastereomers (3S, 4R, 6R)- or (3R, 4S, 6S)-diastereomer, present in said composition is about 1:1. When a composition of the invention has a diastereomeric ratio of about 100%:0%, it should be understood that the composition comprises essentially only the (3R, 4R, 6R)-diastereomer of a compound of general formula (I), (compound of formula (III)). Thus, the composition of the present invention may comprise any mixture of (3R, 4R, 6R)-diastereomer of a compound of general formula (I) (compound of formula (III)) with one or more of its diastereomers ((1S; 4R, 6R)- or (3R, 4S, 6S)-diastereomers), such as for example a composition having a diatereomeric ratio of 50%:50%, 70%:30%, 80%:20%, 90%:10%, 95%:5%, 97%: 3%, 99%:1% or 100%:0%. In some embodiments of the invention, said diastereomeric ratio is at least 97%:3%.

Thus, in another embodiment when ===== indicates a single bond, said diastereomeric ratio indicates the percentage ratio between (1R, 3R, 4R, 6R)-diastereomer of a compound of general formula (I') (compound of formula (IV)) and each of (1S, 3R, 4R, 6R)-, (1R, 3S, 4S, 6S), (1R, 3S, 4R, 6R)-, (1S, 3S, 4R, 6R)-, (1R, 3R, 4S, 6S)— or (1S, 3R, 4S, 6S)-diastereomers, all of which (together or individually) may be present in said composition of the invention.

When a composition of the invention has a diastereomeric ratio of 50%:50%, it should be understood that the ratio between the (1R, 3R, 4R, 6R)-diastereomer of a compound of general formula (I') (compound of formula (IV)) and any one of the diastereomers (1S, 3R, 4R, 6R)-, (1R, 3S, 4S, 6S), (1R, 3S, 4R, 6R)-, (1S, 3S, 4R, 6R)-, (1R, 3R, 4S, 6S)— or (1S, 3R, 4S, 6S)-diastereomer, present in said composition is about 1:1. When a composition of the invention has a diastereomeric ratio of about 100%:0%, it should be understood that the composition comprises essentially only the (1R, 3R, 4R, 6R)-diastereomer of a compound of general formula (I') (compound of formula (IV)). Thus, the composition of the present invention may comprise any mixture of (1R, 3R, 4R, 6R)-diastereomer of a compound of general formula (I') (compound of formula (IV)) with one or more of its diastereomers ((1S, 3R, 4R, 6R)-, (1R, 3S, 4S, 6S), (1R, 3S, 4R, 6R)-, (1S, 3S, 4R, 6R)-, (1R, 3R, 4S, 6S)— or (1S, 3R, 4S, 6S)-diastereomers), such as for example a composition having a diatereomeric ratio of 50%:50%, 70%:30%, 80%:20%, 90%:10%, 95%:5%, 97%:3%, 99%: 1% or 100%:0%. In some embodiments of the invention, said diastereomeric ratio is at least 97%:3%.

In yet a further embodiment when ===== indicates a single bond, said diastereomeric ratio indicates the percentage ratio between (1S, 3R, 4R, 6R)-diastereomer of a compound of general formula (I') (compound of formula (IV)) and each of (1R, 3R, 4R, 6R)-, (1S, 3S, 4S, 6S), (1R, 3S, 4R, 6R)-, (1S, 3S, 4R, 6R)- or (1S, 3R, 4S, 6S)-diastereomers, all of which (together or individually) may be present in said composition of the invention.

When a composition of the invention has a diastereomeric ratio of 50%:50%, it should be understood that the ratio between the (1S, 3R, 4R, 6R)-diastereomer of a compound of general formula (I') (compound of formula (IV)) and any one of the diastereomers (1R, 3R, 4R, 6R)-, (1S, 3S, 4S, 6S), (1R, 3S, 4R, 6R)-, (1S, 3S, 4R, 6R)-, (1R, 3R, 4S, 6S)- or (1S, 3R, 4S, 6S)-diastereomer, present in said composition is about 1:1. When a composition of the invention has a diastereomeric ratio of about 100%:0%, it should be understood that the composition comprises essentially only the (1S, 3R, 4R, 6R)-diastereomer of a compound of general formula (I') (compound of formula (IV)). Thus, the composition of the present invention may comprise any mixture of (1S, 3R, 4R, 6R)-diastereomer of a compound of general formula (I') with one or more of its diastereomers ((1S, 3R, 4R, 6R)-, (1R, 3S, 4S, 6S), (1R, 3S, 4R, 6R)-, (1S, 3S, 4R, 6R)-, (1R, 3R, 4S, 6S)— or (1S, 3R, 4S, 6S)-diastereomers), such as for example a composition having a diatereomeric ratio of 50%:50%, 70%:30%, 80%:20%, 90%:10%, 95%: 5%, 97%:3%, 99%:1% or 100%:0%. In some embodiments of the invention, said diastereomeric ratio is at least 97%: 3%.

The term "diatereomeric excess" as used herein is meant to encompass the subtraction of the mole fraction of one diastereoisomer ($D_1$) from the mole fraction of another diastereoisomer ($D_2$) in a composition, i.e. $D_1$-$D_2$. This term may alternatively relate to the percent diastereoisomer excess as $100\%*(D_1$-$D_2)$.

Thus, in one embodiment when ===== indicates a double bond, said diastereomeric excess indicates the excess in a composition of the invention of (3R, 4R, 6R)-diastereomer of a compound of general formula (I) with respect to each of (3S, 4R, 6R)-, or (3R, 4S, 6S)-, diastereomer of compound of general formula (I), all of which (together or individually) may be present in said composition of the invention.

When the diastereomeric excess of a composition of the invention is 0% the mole fraction of (3R, 4R, 6R)-diastereomer of a compound of general formula (I), is essentially equal to the mole fraction of any one of (3S, 4R, 6R)-, or (3R, 4S, 6S)-diastereomer of compound of general formula (I). When the diastereomeric excess of a composition of the invention is 100% the composition comprises substantially only the (3R, 4R, 6R)-diastereomer of a compound of general formula (I). Thus, the composition of the present invention may comprise any mixture of (3R, 4R, 6R)-diastereomer of a compound of general formula (I) with one or more of its diastereomers ((3S, 4R, 6R)-, or (3R, 4S, 6S)-diastereomers), such as for example a composition having a diastereomeric excess of 0%, 5%, 10%, 20%, 30%, 50%, 80%, 90%, 95%, 97%, 98%, 99%, or 100%. In some embodiments of the invention, said diastereomeric excess is at least 97%.

In another embodiment when ===== indicates a single bond, said diastereomeric excess indicates the excess in a composition of the invention of (1R, 3R, 4R, 6R)-diastereomer of a compound of general formula (I') (compound of formula (IV)) with respect to each of (1S, 3R, 4R, 6R)-, (1R, 3S, 4S, 6S), (1R, 3S, 4R, 6R)-, (1S, 3S, 4R, 6R)-, (1R, 3R, 4S, 6S)- or (1S, 3R, 4S, 6S)-diastereomers, all of which (together or individually) may be present in said composition of the invention.

When the diastereomeric excess of a composition of the invention is 0% the mole fraction of (1R, 3R, 4R, 6R)-diastereomer of a compound of general formula (I') (compound of formula (IV)), is essentially equal to the mole fraction of any one of (1S, 3R, 4R, 6R)-, (1R, 3S, 4S, 6S), (1R, 3S, 4R, 6R)-, (1S, 3S, 4R, 6R)-, (1R, 3R, 4S, 6S)- or (1S, 3R, 4S, 6S)-diastereomers. When the diastereomeric excess of a composition of the invention is 100% the composition comprises substantially only the (1R, 3R, 4R, 6R)-diastereomer of a compound of general formula (I') (compound of formula (IV)). Thus, the composition of the present invention may comprise any mixture of (1R, 3R, 4R, 6R)-diastereomer of a compound of general formula (I') (compound of formula (IV)) with one or more of its diastereomers ((1S, 3R, 4R, 6R)-, (1R, 3S, 4S, 6S), (1R, 3S, 4R, 6R)-, (1S, 3S, 4R, 6R)-, (1R, 3R, 4S, 6S)- or (1S, 3R, 4S, 6S)-diastereomers), such as for example a composition having a diastereomeric excess of 0%, 5%, 10%, 20%, 30%, 50%, 80%, 90%, 95%, 97%, 98%, 99%, or 100%. In some embodiments of the invention, said diastereomeric excess is at least 97%.

In yet another embodiment ===== when indicates a single bond, said diastereomeric excess indicates the excess in a composition of the invention of (1S, 3R, 4R, 6R)-diastereomer of a compound of general formula (I') (compound of formula (IV)) with respect to each of (1R, 3R, 4R, 6R)-, (1S, 3S, 4S, 6S), (1R, 3S, 4R, 6R)-, (1S, 3S, 4R, 6R)-, (1R, 3R, 4S, 6S)- or (1S, 3R, 4S, 6S)-diastereomers, all of which (together or individually) may be present in said composition of the invention.

When the diastereomeric excess of a composition of the invention is 0% the mole fraction of (1S, 3R, 4R, 6R)-diastereomer of a compound of general formula (I') (compound of formula (IV)), is essentially equal to the mole fraction of any one of (1R, 3R, 4R, 6R)-, (1S, 3S, 4S, 6S), (1R, 3S, 4R, 6R)-, (1S, 3S, 4R, 6R)-, (1R, 3R, 4S, 6S)- or (1S, 3R, 4S, 6S)-diastereomers. When the diastereomeric excess of the invention is 100% the composition comprises substantially only the (1S, 3R, 4R, 6R)-diastereomer of a compound of general formula (I') (compound of formula (IV)). Thus, the composition of the present invention may comprise any mixture of (1S, 3R, 4R, 6R)-diastereomer of a compound of general formula (I') (compound of formula (IV)) with one or more of its diastereomers ((1R, 3R, 4R, 6R)-, (1S, 3S, 4S, 6S), (1R, 3S, 4R, 6R)-, (1S, 3S, 4R, 6R)-, (1R, 3R, 4S, 6S)- or (1S, 3R, 4S, 6S)-diastereomers), such as for example a composition having a diastereomeric excess of 0%, 5%, 10%, 20%, 30%, 50%, 80%, 90%, 95%, 97%, 98%, 99%, or 100%. In some embodiments of the invention, said diastereomeric excess is at least 97%.

In another embodiment, a composition of the invention has an enantiomeric excess of between about 100% to more than about 0%.

The term "enantiomeric excess" (also denoted "ee") is meant to encompass a percent excess of an enantiomer ($E_1$ or $E_2$) over the racemic mixture (1:1 mixture of $E_1$ and $E_2$), in accordance with eq. 1 below:

$$ee = \frac{|E_1 - E_2|}{E_1 + E_2} * 100 = |\% E_1 - \% E_2| \quad (\text{eq. 1})$$

Thus, where referring to ee value of 100% of, for example, enantiomer $E_1$ it should be understood to encompass substantially only one enantiomer ($E_1$). When referring to ee value of more than about 0% of, for example, enantiomer $E_1$ it should be understood to encompass non racemic mixtures of $E_1$ and $E_2$.

In one embodiment, when ===== indicates a double bond, said ee indicates the percentage excess between the (3R, 4R, 6R) stereoisomer of a compound of general formula (I) or (III), and its enantiomer (3S, 4S, 6S).

In another embodiment, when ===== indicates a single bond, said ee indicates the percentage excess between the (1R, 3R, 4R, 6R) stereoisomer of a compound of general formula (I') or (IV), and its enantiomer (1S, 3S, 4S, 6S).

In yet a further embodiment, when ===== indicates a single bond, said ee indicates the percentage excess between the (1S, 3R, 4R, 6R) stereoisomer of a compound of general formula (I') or (IV), and its enantiomer (1R, 3S, 4S, 6S).

In some embodiments, $R_1$ is —$R_2OR_3$, wherein $R_2$ and $R_3$ are as defined hereinabove. In a further embodiment $R_2$ is —$CH_2$—. In some other embodiments $R_6$ is H and $R_7$ is —$OR_8$, wherein $R_8$ is a straight or branched $C_1$-$C_5$ alkyl. In other embodiments $R_7$ is H and $R_6$ is —$OR_8$, wherein $R_8$ is a straight or branched $C_1$-$C_5$ alkyl. In some other embodiments, $R_6$ and $R_7$ are each independently —$OR_8$, wherein $R_8$ is a straight or branched $C_1$-$C_5$ alkyl. In some other embodiments $R_9$ is an optionally substituted branched $C_6$-$C_{12}$ alkyl.

As used herein, the term "alkyl" refers to a straight or branched chain hydrocarbon having from one to five carbon atoms, or from one to seven carbon atoms, or from five to nine carbon atoms, or from six to twelve carbon atoms. Examples of "alkyl" as used herein include, but are not limited to, methyl, ethyl, propyl, n-butyl, n-pentyl, isobutyl, and isopropyl, tert-butyl, and the like.

As used herein the term "alkylene" refers to a saturated, divalent, branched or straight hydrocarbon group having from one to five carbon atoms. Non-limiting examples of $C_{1-5}$-alkylene groups include, methylene, ethylene, 1,2-propylene, 1,3-propylene, butylene, isobutylidene, pentylene, hexylene and the like.

As used herein the term "ester" is meant to encompass an —COOR group wherein R is an alkyl as defined herein above.

A used herein the term "ether" refers to an —R'OR group, wherein R' is a $C_1$-$C_7$ straight or branched alkylene group and R is a $C_1$-$C_7$ straight or branched alkyl group.

As used herein, the term "alkoxy" refers to an RO— group, where R is alkyl as defined above.

As used herein the term "$C_1$-$C_7$ amide" refers to a monoalkyl amide (—CONHR) or dialkyl amide (—CONRR'), wherein R and R' are independently a $C_1$-$C_7$ straight or branched alkyl.

As used herein the term "$C_1$-$C_5$ amine" refers to an —NHR or —NRR' group wherein R and R' are independently a $C_1$-$C_5$ straight or branched alkyl.

As used herein the term "$C_1$-$C_5$ alkoxy" refers to a —OR group wherein R is a $C_1$-$C_5$ alkyl.

As used herein the term "$C_1$-$C_5$ acyl" refers to a —C(=O)R group wherein R is a straight or branched $C_1$-$C_5$ alkyl.

The term "optionally substituted" as used herein means that the groups in question are either unsubstituted or substituted with one or more of the substituents such as for example those specified above, phenyl, substituted phenyl, aryl, heteroaryl, cycloalkyl, heterocycloalkyl, halogen (—F, —Cl, —Br, —I). When the groups are substituted with more than one substituent the substituents may be the same or different and said substitution may occur at any position on the substituted group (i.e. at a terminal or any mid-chain position or both).

In an embodiment of the present invention, said compound of formula (II) is the following compound (HU-433):

(1)

In some embodiments of the invention said composition is a pharmaceutical composition. When referring to pharmaceutical compositions comprising a compound of the subject invention it should be understood to encompass admixtures of compounds of the invention, with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy. Such methods include the step of bringing in association compounds used in the invention or combinations thereof with any auxiliary agent.

Auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use.

For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

The inventors of the present application found that a composition comprising substantially HU-433, retained the CB2 specificity, with nearly 2-fold higher binding potency, and respective 1000- and 100-fold higher in vitro and in vivo skeletal activities, compared to HU-308. Thus, in some embodiments of the present invention there is provided a composition capable of binding to a CB receptor.

The term "CB receptor" is meant to encompass a cannabinoid G-protein coupled receptor, defined by their capability to bind to cannabinoids and/or endocannabinoids. In some embodiments said receptor is a CB1 (cannabinoid receptor Type 1) and/or CB2 receptor (cannabinoid receptor Type 2). In other embodiments said receptor is a CB2 receptor (cannabinoid receptor Type 2).

CB1 subtype receptor is mainly expressed in the brain, lungs, liver and kidneys. CB2 subtype receptor is mainly expressed in the immune system and in hematopoietic cells.

When referring to "binding" of a composition of the invention to a CB receptor it is meant to include any type of association between a composition of the invention and a CB receptor, which may activate said bound receptor.

In some embodiments said composition is capable of being bound to CB1 and CB2 receptors. When both receptors are capable of being bound by a composition of the invention, the extent of binding may be identical or different. In some embodiments a composition of the invention binds to CB2 receptor to a greater extent as compared with the binding to CB1 receptor. Thus resulting in an activation of CB2 receptor to a greater amount compared with activation of CB1 receptor. In some embodiments activation of the CB2 receptor by a composition of the invention is at least 10 times higher than the activation of the CB1 receptor. In other embodiments composition of the invention is capable of binding to CB2 receptor.

In other embodiments said binding of a CB receptor by a composition of the invention is associated with a beneficial therapeutic effect, such as the treatment of a disease or disorder. Examples of disease wherein a beneficial therapeutic effect is evident by activation of CB receptor (in some embodiments, with low or no activation of CB1 receptor) are: inflammation (Benito et al., *Brit. J. Pharmacol.* 153, 277-285, 2008), pain, allergies, neurological diseases— multiple sclerosis (Docagne et al., *Expert Opin. Therapeutic Targets,* 12, 185-185, 2008), Alzheimer's (Benito et al., ibid), amyotropic lateral sclerosis (Kim et al., *Eur J Pharmacol,* 542, 100-105, 2006), HIV-induced encephalitis (Benoto et al., *J. Neurosci.* 25, 2530-2536, 2005), neuropathic pain (Zhang et al., *Eur, J. Neurosci,* 17, 2750-2754, 2003); Huntington disease (Sagredo et al. *Glia,* 57, 1154-1167 2009); Parkinson (Papa, S M. *Exp. Neurol.* 211, 334-338, 2008); Schizophrenia (Agid et al. *Expert Opin Emerg Drugs.*, 13, 479-95, 2008). in liver diseasesin particular fibrogenesis associated with chronic liver diseases, ischaemia/reperfusion (I/R)-induced liver injury (Lotersztein et al., *Brit. J. Pharmacol.* 153, 286-289, 2008) and hepatic encephalopathy-associated with acute liver failure (Magen et al. *Current Pharmaceutical Design.* 14, 2362-2369, 2008), cerebral ischemic-reperfusion injury (Zhang et al., *Neurosci.* 152, 753-760, 2008); in cancer especially of hematopoietic origin (lymphoma and acute lymphocytic leukaemia), retinal vascularization, endometritis; appetite related disorders, metabolic syndrome, diabetes, and obesity. In some embodiments said disease or disorder is selected from inflammation, pain, allergies, neurological and neurodegenerative diseases, liver diseases, cerebral ischemic-reperfusion injury, cancer, retinal vascularization, endometritis, appetite related disorders, metabolic syndrome, diabetes, atherosclerosis and disorders related to anti-fibrinogenic effects and emesis or any combinations thereof.

In other embodiments a composition of the invention is for use in the stimulation of bone growth, bone mass, bone repair or prevention of bone loss.

In some other embodiments a composition of the invention is for the treatment of a disease or a disorder selected from osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer and osteomyelitis, or any combinations thereof. In some embodiments said disease or disorder is selected from osteopenia and osteoporosis.

In a further aspect, the present invention provides a use of a composition of the invention, for the manufacture of a medicament for activating a CB receptor.

In yet a further aspect, the invention provides a use a composition of the invention, for the manufacture of a medicament for stimulation of bone growth, bone mass, bone repair or prevention of bone loss.

In another aspect, the invention provides a use a composition of the invention, for the manufacture of a medicament for the treatment of a disease or a disorder selected from osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof.

In a further aspect, the invention provides a method for activating a CB receptor in a subject in need thereof, said method comprising administering to said subject a therapeutically effective amount of a composition of the invention.

In yet a further aspect the invention provides a method of stimulation of bone growth, bone mass, bone repair or prevention of bone loss, said method comprising administering to a subject in need thereof a therapeutically effective amount of a composition of the invention.

The term "treatment" as used herein refers to the administering of a therapeutic amount of the composition of the present invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

As used herein, the term "effective amount" means that amount of a composition of the invention that will elicit the biological or medical response of a tissue, system, animal or human that is being sought, for instance, by a researcher or clinician. The effective amount for purposes disclosed herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The invention further provides a composition comprising compound (1), said composition having a melting point of 44-45° C. and optical rotation of $[\alpha]_D = -115°$.

In a further aspect of the invention there is provided a method for preparing a compound of formula (II), said method comprising:

esterification of a compound of formula (V) with an acyl chloride to obtain compound (VI):

wherein acyl chloride may be any alkyl chloride for example pivaloyl chloride;

oxidation of compound (VI) to obtain 4-oxo-substituted compound (VII):

reduction of 4-oxo-substituted compound (VII) to the 4-hydroxy-substituted compound (VIII):

it is noted that such a reduction may give raise to both equatorial and axial hydroxyl substitution on position 4 of the bicyclic ring, with possible preference to the less sterically hindered substitution, such as for example the equatorial substitution.

condensation of 4-hydroxy-substituted compound (VIII) with compound (IX) to obtain condensed compound (X):

without wishing to be bound by theory this condensation will occur preferably at the equatorial position which is less sterically hindered due to the position of the dimethyl bridge.

reduction of ester group of condensed compound (X) to obtain compound of formula (II):

Such a reduction may also be obtained by hydrogenation of the ester group with agents such as for example $LiAlH_4$ to obtain the corresponding hydroxyl group. It is noted that the substituents $R_2$, $R_3$, $R_6$, $R_7$, and $R_9$ are all as defined herein above.

The present invention further concerns a method for the synthesis of HU-433, the method comprising:

1) esterification of (−) myrtenol $[\alpha]_D=-51°$ with pivaloyl chloride in dry pyridine, thereby obtaining myrtenyl pivalate;

2) oxidation of myrtenyl pivalate with $CrO_3$ and tBuOOH in $CH_3CN$ to obtain the 4-oxomyrtenyl pivalate having m.p. 35° C., $[\alpha]_D=-162°$;

3) reduction of 4-oxomyrtenyl pivalate with $NaBH_4$ in ethanol to obtain 4-hydroxymyrtenyl pivalate;

4) condensation of 4-hydroxymyrtenyl pivalate with 5-dimethylheptyl-resorcinol (5-DMH-resorcinol), in the presence of pTSA, to obtain 2-(3-myrtenyl pivalate)-5-dimethylheptyl resorcinol;

5) methylation of 2-(3-myrtenyl pivalate)-5-dimethylheptyl resorcinol with methyl iodide and potassium carbonate to give 2-(3-myrtenyl pivalate)-5-dimethylheptyl dimethylresorcinol (HU-433 pivalate);

6) reaction of 2-(3-myrtenyl pivalate)-dimethylheptyl dimethyl resorcinol (HU-433 pivalate) with $LiAlH_4$ to yield the desired (−)-2-(3-myrtenyl)-5-dimethylheptyl resorcinol (HU-433), (−) isomer with m.p. 44-45° C., $[\alpha]_D=-115°$.

The present invention further concerns compounds obtainable by the above method.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", should be understood to imply the inclusion of a stated integer or step or group of integers or steps but not the exclusion of any integer or step or group of integers and steps.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Example 1

Synthesis of HU-433

1. Preparation of Myrtenyl Pivalate

Pivaloyl chloride (8 g, 67 mmol) was added slowly to a solution of myrtenol (commercial myrtenol; Aldrich CAS#19894-97-4), $[\alpha]_D=-51°$ (5 g, 33 mmol) in dry pyridine (25 ml), with cooling in ice bath. The mixture was stirred overnight at room temperature. Then the mixture was diluted with ether (25 ml) and ice water was added, the organic layer collected and washed with 10% HCl several times, then with $NaHCO_3$, dried over $Na_2SO_4$ and evaporated to give 7.17 g (91%) colorless oil.

2. Preparation of 4-Oxomyrtenyl Pivalate:

For the preparation of 4-oxomyrtenyl pivalate, CrO3 (1.06 g, 10.6 mmol) was dissolved in $CH_3CN$ (35 ml) and stirred at 0° C. Then t-BuOOH (17.5 ml 70%/$H_2O$, 126 mmol) was added followed by the immediate addition of a solution of myrtenyl pivalate (5 g, 20 mmol) in $CH_3CN$ (38 ml). The reaction mixture was brought to room temperature and was stirred for 1 h. The reaction mixture was diluted with ether, and 10% $Na_2SO_3$ in water (130 ml) was added. The mixture was extracted several times with ether, dried and evaporated. The crude mixture was purified by silica gel column chromatography (0-10% ether in petroleum ether) to give an oil that crystallized from pentane to give 4-oxo-myrtenyl pivalate (0.9 g, 19%) m.p. 35° C., $[\alpha]_D=-162°$.

3. Preparation of 4-Hydroxymyrtenyl Pivalate:

4-Oxo-myrtenyl pivalate (1 g, 4 mmol) was dissolved in ethanol (15 ml). $NaBH_4$ (0.2 g, 5.3 mmol) was added slowly and the resulting suspension was stirred at room temperature for 15 min. The ethanol was evaporated, then ether and water were added. The organic layer was separated, dried and evaporated to give a colorless oil (0.92 g, 91%).

4. Condensation of 4-Hydroxymyrtenyl Pivalate with DMH-Resorcinol:

To a solution of dry pTSA (0.16 g, 0.96 mmol) and 1,1-DMH-resorcinol (0.86 g, 3.44 mmol) in dry dichloromethane (125 ml) and under argon atmosphere, was added slowly a solution of 4-hydroxy-myrtenyl pivalate (0.88 g, 3.49 mmol) in dry dichloromethane (30 ml). The mixture was stirred at room temperature for 1.5 h. A saturated $NaHCO_3$ solution was added and the organic layer was then washed twice with water, dried and evaporated. The residue was purified by column chromatography on silica gel in ether/pet.ether (5:95) to give 0.71 g (43%) 2-(3-myrtenyl pivalate)-5-dimethylheptyl-resorcinol, a colorless oil.

5. Methylation:

Methyl iodide (0.75 ml, 12 mmol) was added to a solution of 2-(3-myrtenyl pivalate)-5-dimethylheptyl resorcinol (0.71 g, 1.51 mmol) and $K_2CO_3$ (1.6 g, 12 mmol) in dry DMF (5 ml). After stirring at room temperature for 24 h, the mixture was diluted with water (40 ml) and extracted with ether. The organic layer was washed with water, dried and evaporated. Purification by column chromatography on silica gel with etherpetroleum ether (5:95) gave 0.51 g (67%) 2-(3-myrtenyl pivalate)-5-dimethylheptyl resorcinol (HU-433, pivalate) a colorless oil 6. Preparation of HU-433

HU-433 pivalate (0.35 g, 0.7 mmol) in dry ether (20 ml) was added slowly, under argon to a suspension of LiAlH4 (64 mg, 1.68 mmol) an dry ether (5 ml). The mixture was refluxed for 2 h. The excess LiAlH$_4$ was destroyed with ethyl acetate followed by a saturated solution of MgSO$_4$ until a clear ether solution was obtained. The ether layer was decanted, dried and evaporated. The product precipitated out from pentane to give HU-433, m.p. 44-45° C., $[\alpha]_D = -115°$ HU-433 spectral data: $^1$H-NMR (CDCl$_3$): 3.741 (s, 6H CH3O—), 3.998 (t, J=2.1 Hz, 1H allylic), 4.069 (d, J=5.7 Hz, 2H, —CH2OH), 5.704 (t, J=1.2, 1H, olefinic) 6.483 (s, 2H, aromatic). MS calc/found: m/z 414.37/437.27 (m+Na).

Example 2

Binding Affinity of HU-433 Vs. HU-308 to CB1 and CB2 Cannabinoid Receptors

Binding of HU-308 to the CB1 and CB2 cannabinoid receptors was assayed (see Hanus et al, 1999), showing $K_i$ value of 22.7 nM. Binding of HU-433 was found to be significantly more potent, having $K_i$ value of 12.2 nM.

For CB1 receptor binding, synaptosomal membranes were prepared from the brains of Sabra rats by homogenization and gradient centrifugation (Devane et al, 1992). For CB2 receptor binding assay, COS-7 cells were transfected with plasmids containing CB2 cDNA, and crude membranes were prepared (Munro et al, 1993).

The high affinity receptor probe, [$^3$H]HU-243 (Tocris Cookson Ltd., United Kingdom), with a dissociation constant of 45±7 pM for the CB1 receptor, was incubated with synaptosomal membranes (3-4 µg) for CB1 assay or transfected cells for the CB2 assay, for 90 min at 30° C. with different concentrations of the assayed ligands or with the vehicle alone (fatty acid-free bovine serum albumin at a final concentration of 0.5 mg/ml).

Bound and free radioligands were separated by centrifugation. The data were normalized to 100% of specific binding, which was determined with 50 nM unlabeled HU-243.

Hanus et al., showed that HU-308 did not bind to CB1 receptor however showed potent binding to CB2 receptor (Table 1). In the present example it was shown that HU-433 did not bind to CB1 receptor. The binding of HU-433 to CB2 receptor was nearly twice more potent compared to HU-308 (Table 3).

TABLE 3

Binding of HU-433 and HU-308 to CB1 and CB2 receptors

| | Ki Receptor | |
|---|---|---|
| Ligand | CB1 | CB2 |
| HU-433 | >20 µM | 12.2 nM |
| HU-308 | >10 µM | 22.7 nM |

Example 3

Comparative Skeletal Activity of HU-433 and HU-308

Figure 1A:
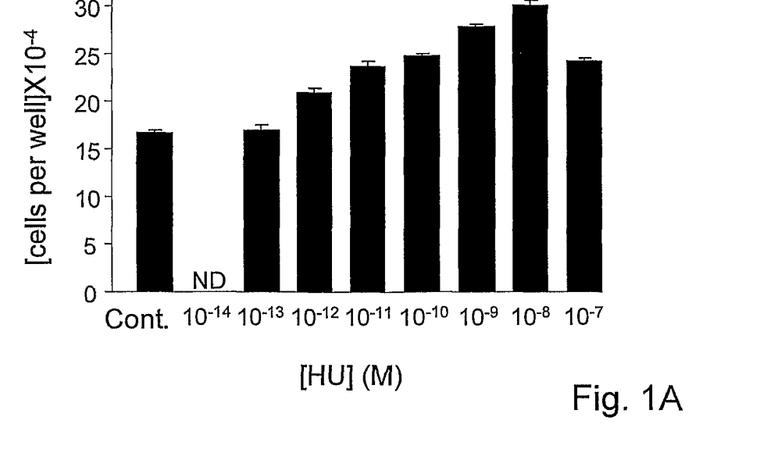
FIGS. 1A-1B shows column diagram describing the stimulation of MC3T3 E1 osteoblastic cell number by a compound of the present invention (i.e. HU-433) (FIG. 1A) and HU-308 (FIG. 1B) (shown as [cell per well]×$10^{-4}$ as a function of compound concentration (M). Data is mean±S.E. obtained in 3 culture wells per condition). ND, not done.
Figure 1B:
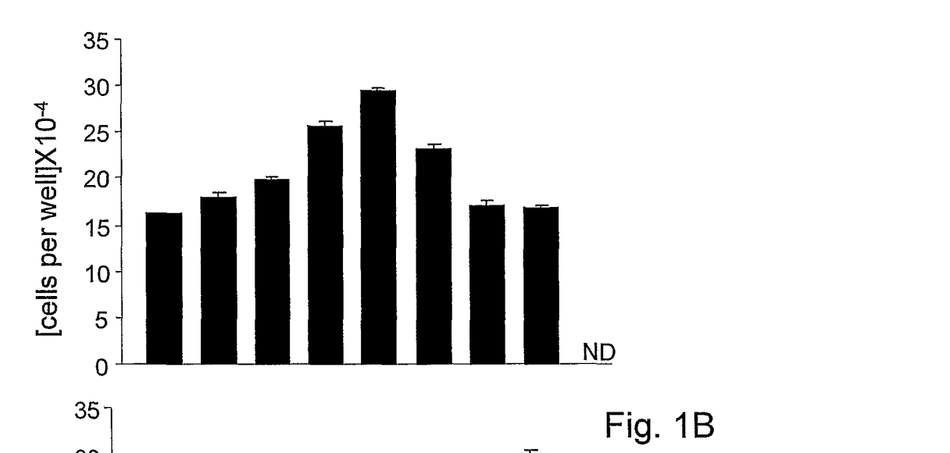

Osteoblastic MC3T3 E1 cells were cultured as reported in Miguel et al, 2005. For the last 46 hours in culture the cell were incubated with HU-433 or HU-308 added as a DMSO solution. Control cultures were treated only with the DMSO solvent (Ofek et al, 2006). In these cells, HU-433 and HU-308 doubled cell number at respective ligand concentrations of $10^{-11}$ M and $10^{-8}$ M, indicating that in the assay of HU-433 was a 1000-fold more active compared to HU-308 (FIGS. 1A and 1B). Typical of this assay system, the dose-response curves are bell shaped (Miguel et al, 2005), with the peak stimulation of cell number followed by reversal of the effect to baseline levels.

Based on the in vitro screening, the in vivo skeletal activity of HU-433 and HU-308 was analyzed in an ovariectomy (removal of ovaries; OVX) mouse model, the most widely used animal model for osteoporosis. Using this experimental system for testing bone anabolic activity, OVXed mice are left untreated to allow for bone loss to occur, followed by a treatment period intended for reversal of the bone loss (Alexander et al, 2001).

Figure 2A:
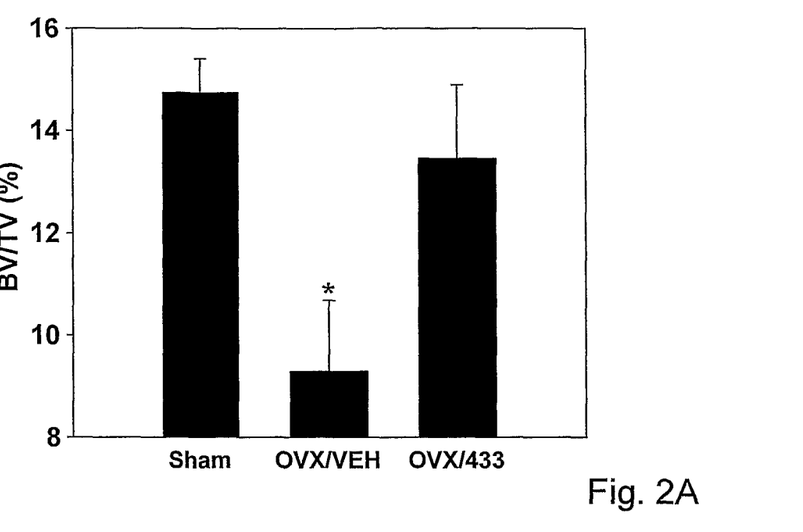
FIGS. 2A-2B shows column diagram describing the rescue of ovariectomy (OVX)-induced loss of trabecular bone volume density (BV/TV) by a compound of the present invention (i.e. HU-433) and HU-308. Treatment commenced 6 weeks after OVX, to allow initial bone loss, and consisted of 6-week intraperitoneal administration of: 0.2 mg/Kg/day HU-433 (FIG. 2A); 20 mg/Kg/day HU-308 (FIG. 2B). μCT analysis. Data are mean±S.E. obtained in 6 mice per condition. (*) p<0.05.
Figure 2B:
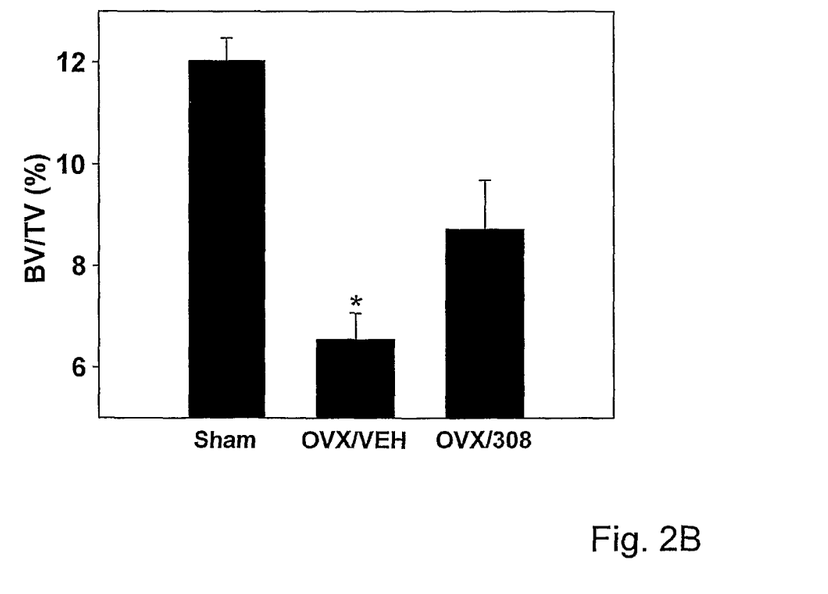

A micro-computed tomographic (µCT) analysis of L3 vertebrae indicated that HU-433, at 0.2 mg/Kg/day for 6 weeks significantly rescued almost the entire OVX-induced trabecular bone loss, whereas HU-308 reversed only 50% of the bone loss, and only at 20 mg/Kg/day for 6 weeks (FIGS. 2A and 2B). Thus, in vivo, HU-433 is at least 100-fold more active than HU-308 (at a 100 fold increase it only caused 50% of the HU-433 effect). The effect of HU-433 in above in vivo test system is substantially greater than the reversal of bone volumetric density by parathyroid hormone (1-34), the only clinically approved bone anabolic agent (Alexander et al, 2001).

What is claimed is:

1. A composition comprising the (3R, 4R, 6R)-diastereomer of a compound of general formula (II):

wherein

===== is a double bond;

$R_1$ is independently selected from —$R_2OR_3$, —C(=O)$R_4$, and —OC(=O)$R_5$;

$R_2$ is a $C_1$-$C_5$ straight or branched alkylene;

$R_3$ is selected from the group consisting of H, —C(=O)OH, straight or branched $C_1$-$C_5$ alkyl, straight or branched $C_1$-$C_5$ acyl, and straight or branched $C_1$-$C_5$ amide;

$R_4$, and $R_5$ are independently selected from the group consisting of H, OH, straight or branched $C_1$-$C_5$ alkyl, straight or branched $C_1$-$C_5$ alkoxy, and straight or branched $C_1$-$C_5$ amine;

$R_6$ and $R_7$ are each independently selected from H, and —$OR_8$ wherein $R_8$ is a straight or branched $C_1$-$C_5$ alkyl, provided that at least one of $R_6$ and $R_7$ is different than H; and $R_9$ is independently selected from an optionally substituted straight or branched $C_6$-$C_{12}$ alkyl, an optionally substituted straight or branched $C_5$-$C_9$ alkoxy, and an optionally substituted straight or branched $C_1$-$C_7$ ether.

2. The composition according to claim 1, wherein $R_1$ is —$R_2OR_3$.

3. The composition according to claim 1, wherein $R_1$ is —$R_2OR_3$, and $R_2$ is —$CH_2$—.

4. The compound according to claim 1, wherein $R_6$ is H, $R_7$ is —$OR_8$, and $R_8$ is a straight or branched —$C_1$-$C_5$ alkyl.

5. The compound according to claim 1, wherein $R_7$ is H, $R_6$ is —$OR_8$, and $R_8$ is a straight or branched —$C_1$-$C_5$ alkyl.

6. The composition according to claim 1, wherein $R_6$ and $R_7$ are each independently —$OR_8$, and $R_8$ is a straight or branched —$C_1$-$C_5$ alkyl.

7. The composition according to claim 1, wherein $R_9$ is an optionally substituted branched —$C_6$-$C_{12}$ alkyl.

8. The composition according to claim 1, wherein the compound of formula (II) is:

9. The composition according to claim 1, wherein the composition is a pharmaceutical composition.

10. The composition according to claim 1, capable of binding to a CB receptor.

11. The composition according to claim 1, capable of binding to a CB2 receptor.

12. A method of stimulating bone growth, bone mass, bone repair or prevention of bone loss, comprising administering to a subject in need thereof, a therapeutically effective amount of the composition according to claim 1.

13. A method for treating osteopenia and osteoporosis, comprising administering to a subject in need thereof, a therapeutically effective amount of the composition according to claim 1.

14. A method for preparing a compound of formula (II) as defined in claim 1, comprising:

esterifying a compound of formula (V) with an acyl chloride to obtain compound (VI):

oxidizing compound (VI) to obtain 4-oxo-substituted compound (VII):

reducing 4-oxo-substituted compound (VII) to the 4-hydroxy-substituted compound (VIII):

condensing 4-hydroxy-substituted compound (VIII) with compound (IX) to obtain condensed compound (X):

and reducing an ester group of condensed compound (X) to obtain the compound of formula (II):

* * * * *